United States Patent [19]

Nakayama et al.

[11] Patent Number: 4,607,114
[45] Date of Patent: Aug. 19, 1986

[54] NOVEL PLATINUM COMPLEXES

[75] Inventors: Yuya Nakayama, Omiya; Kenji Iwata, Kuki; Katsutoshi Takahashi, Tokyo, all of Japan

[73] Assignee: Nippon Kayaku Kabushiki Kaisha, Japan

[21] Appl. No.: 661,433

[22] Filed: Oct. 16, 1984

[30] Foreign Application Priority Data

Oct. 19, 1983 [JP] Japan .................. 58-194358

[51] Int. Cl.$^4$ .......................................... C07F 15/00
[52] U.S. Cl. ................................................. 556/137
[58] Field of Search ...................... 260/429 R; 556/137

[56] References Cited

U.S. PATENT DOCUMENTS 4,255,347 3/1981 Kidani et al. ................. 260/429 R
4,431,666 2/1984 Bulten et al. ............... 260/429 R X
4,466,924 8/1984 Verbeek et al. ............... 260/429 R
4,482,569 11/1984 Bulten et al. ............... 260/429 R X

FOREIGN PATENT DOCUMENTS 0008936 3/1980 European Pat. Off. ........ 260/429 R

OTHER PUBLICATIONS

Chemical Abstracts 91 116493w (1979).
Chemical Abstracts, 71 34905e (1969).
Chemical Abstracts 73 1997/w (1970).
Chemical Abstracts 81 113304t (1974).
Leh, Francis K. V. and Walter Wolf, *Journal of Pharmaceutical Sciences*, "Platinum Complexes: A New Class of Antineoplastic Agents", vol. 65, No. 3, 315–328 (1976).
Hall et al., *Journal of Inorganic Biochemistry*, "Unsymmetrical C-Substituted Ethylenediamine Platinum Coordination Complexes: Synthesis and Activity Against Mouse Leukemia L1210", vol. 11, 139–149 (1979).

*Primary Examiner*—Helen M. S. Sneed
*Attorney, Agent, or Firm*—Banner, Birch, McKie & Beckett

[57] ABSTRACT

This invention relates to a novel platinum-diamine complexes represented by the general formula:

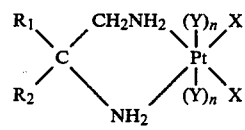

wherein $R_1$ and $R_2$ each represents a lower alkyl group having 1 to 3 carbon atoms or jointly represent an alkylene group having 3 to 6 carbon atoms; two X's each represents a halogen atom,

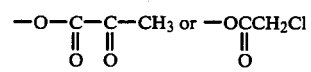

or jointly represent a group represented by

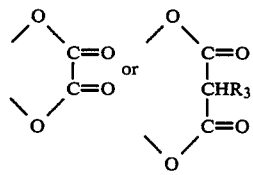

in which $R_3$ is a lower alkyl group or a group represented by —OM (wherein M is an atom which can become a monovalent cation); Y is —OH or a halogen atom; and n is 0 or 1, and n is 1 when $R_1$ and $R_2$ jointly represent an alkylene group having 5 carbon atoms and X is chlorine. The platinum-diamine complex of this invention has an excellent antitumor activity and a lower renal toxicity than cis-Platin now widely used as a carcinostatic as clinical medicine, and is expected as a carcinostatic lowered in toxicity.

13 Claims, No Drawings

NOVEL PLATINUM COMPLEXES

BACKGROUND OF THE INVENTION

It has already been known that certan platinum complexes have a carcinostatic effect [e.g., Journal of Pharmaceutical Sciences, Vol. 65, No. 3, 315-328 (1976) and Journal of Inorganic Biochemistry, 11, 139-149 (1979)].

Among these compounds, cis-dichlorodiammineplatinum (cis-Platin, generic name) has a very excellent carcinostatic effect and is now widely used as clinical medicine. However, this compound is disadvantageous in that it is high in toxicity, particularly in renal toxicity and is very low in water-solubility.

SUMMARY OF THE INVENTION

Accordingly, the present inventors have conducted extensive research and have consequently found that a platinum-diamine complex represented by the general formula (I):

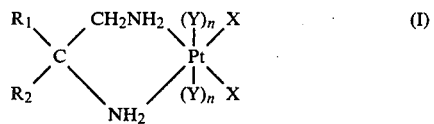

wherein $R_1$ and $R_2$ each represents lower alkyl group having 1 to 3 carbon atoms or jointly represent an alkylene group having 3 to 6 carbon atoms; two X's each represents a halogen atom

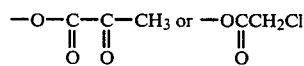

or jointly represent a group represented by

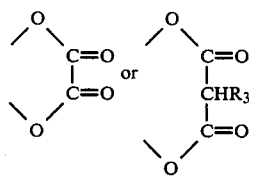

in which $R_3$ is a lower alkyl group or a group represented by —OM (wherein M is an atom which can become a monovalent cation); Y is —OH or a halogen atom; and n is 0 or 1, and n is 1 when $R_1$ and $R_2$ jointly represent an alkylene group having 5 carbon atoms and X is chlorine, has an excellent antitumor effect and at the same time has a lower renal toxicity and a higher water-solubility than cis-Platin. This invention has been accomplished on the basis of this finding.

The object of this invention is to provide a novel platinum-diamine complex having an antitumor activity and a low renal toxicity and a process for producing the same.

DETAILED DESCRIPTION OF THE INVENTION

In the compound represented by the above general formula (I), the lower alkyl group having 1 to 3 carbon atoms for $R_1$ and $R_2$ include methyl group, ethyl group, n-propyl group and isopropyl group. The alkylene group having 3 to 6 carbon atoms formed by combination of $R_1$ and $R_2$ includes trimethylene group, tetramethylene group, pentamethylene group and hexamethylene group. The lower alkyl group for $R_3$ includes methyl group, ethyl group, etc. M in $R_3$ includes hydrogen, monovalent metals such as sodium, potassium and the like, ammonia, etc. The halogen includes chlorine, bromine, iodine and fluorine.

Among the compounds represented by the above general formula (I), typical ones are listed below.
1. cis-Dichloro-1,2-diamino-2-methylpropane platinum.
2. cis-Dichloro-trans-dihydroxy-1,2-diamino-2-methylpropane platinum.
3. cis-Tetrachloro-1,2-diamino-2-methylpropane platinum.
4. cis-Dichloro-1,2-diamino-2-methylbutane platinum.
5. cis-Dichloro-1,2-diamino-2-ethylbutane platinum.
6. cis-Oxalato-1,2-diamino-2-ethylbutane platinum.
7. cis-Dichloro-trans-dihydroxy-1,2-diamino-2-ethylbutane platinum.
8. cis-Tetrachloro-1,2-diamino-2-ethylbutane platinum.
9. cis-2-Ethylmalonato-1,2-diamino-2-ethylbutane platinum.
10. cis-2-Hydroxymalonato-1,2-diamino-2-ethylbutane platinum.
11. cis-Dichloro-trans-dihydroxy-1-amino-1-aminomethylcyclohexane platinum.
12. cis-Tetrachloro-1-amino-1-aminomethylcyclohexane platinum.
13. cis-Oxalato-1-amino-1-aminomethylcyclohexane platinum.
14. Sodium salt of cis-2-hydroxymalonato-1-amino-1-aminomethylcyclohexane platinum.
15. cis-bis(Chloroacetato)-1-amino-1-aminomethylcyclohexane platinum.
16. cis-bis(Pyruvato)-1-amino-1-aminomethylcyclohexane platinum.
17. cis-2-Ethylmalonato-1-amino-1-aminomethyl cyclohexane platinum.
18. cis-Dichloro-1-amino-1-aminomethylcyclopentane platinum.
19. cis-Dichloro-trans-dihydroxy-1-amino-1-aminomethylcyclopentane platinum.
20. cis-Tetrachloro-1-amino-1-aminomethyl cyclopentane platinum.
21. cis-Oxalato-1-amino-1-aminomethylcyclopentane platinum.
22. cis-2-Ethylmalonato-1-amino-1-aminomethylcyclopentane platinum.
23. cis-2-Hydroxymalonato-1-amino-1-aminomethylcyclopentane platinum.

Physicochemical properties of these compounds are shown in Table 1.

TABLE 1

| No. | Appearance | Melting point (°C.) | Solubility in water (mg/ml) | TLC[1] Rf | Molecular formula | | Calcd. % | Found % | IR absorption spectrum (cm$^{-1}$) |
|---|---|---|---|---|---|---|---|---|---|
| 1 | Yellow crystals | 280–285° (decomp.) | 5 | 0.49 | $C_4H_{12}N_2Cl_2Pt$ | C | 13.57 | 13.30 | 3290, 3225, 3125, |
|  |  |  |  |  |  | H | 3.42 | 3.65 | 2980, 1590, 1580, |
|  |  |  |  |  |  | N | 7.91 | 7.80 | 1474, 1460, 1400, |

TABLE 1-continued

| No. | Appearance | Melting point (°C.) | Solubility in water (mg/ml) | TLC[1] Rf | Molecular formula | | Elementary analysis Calcd. % | Found % | IR absorption spectrum (cm$^{-1}$) |
|---|---|---|---|---|---|---|---|---|---|
| | | | | | | Cl | 20.02 | 19.68 | 1380, 1344, 1304, 1268, 1218, 1190, 1140, 1122, 1010, 968, 802, 720 |
| 2 | Light-yellow crystals | 279–281° (decomp.) | >20 | 0.56 | $C_4H_{14}N_2O_2Cl_2Pt$ | C H N Cl | 12.38 3.64 7.22 18.27 | 12.25 3.76 7.15 18.04 | 3570, 3500, 3245, 2900, 2625, 2550, 2475, 2090, 1618, 1568, 1494, 1380, 1358, 1314, 1302, 1212, 1182, 1136, 1060, 1010, 980, 900, 808, 738 |
| 3 | Yellow crystals | 264–265° (decomp.) | >12 | 0.51 | $C_4H_{12}N_2Cl_4Pt$ | C H N Cl | 11.30 2.85 6.59 33.36 | 11.45 2.98 6.57 32.48 | 3475, 3250, 3200, 3100, 2990, 1575, 1560, 1474, 1410, 1340, 1304, 1220, 1200, 1140, 1100, 1020, 980, 888, 820, 760, 720 |
| 4 | Yellowish-white crystals | 271° (decomp.) | 3.5 | 0.70 | $C_5H_{14}N_2Cl_2Pt$ | C H N Cl | 16.31 3.83 7.61 19.26 | 16.41 3.90 7.58 19.40 | 3460, 3250, 3200, 3130, 2980, 2900, 1580, 1465, 1400, 1195, 1130, 800 |
| 5 | Yellow crystals | 281° (decomp.) | >2.5 | 0.63 | $C_6H_{16}N_2Cl_2Pt$ | C H N Cl | 18.86 4.22 7.33 18.55 | 18.71 4.02 7.15 18.63 | 3500, 3245, 3200, 2975, 2890, 1590, 1465, 1390, 1195, 1130, 795, 700 |
| 6 | White crystals | >300° | >5 | 0.58 | $C_8H_{16}N_2O_4Pt$ | C H N | 24.06 4.04 7.02 | 24.28 4.15 6.90 | 3450, 3230, 3160, 2985, 2900, 1708, 1687, 1665, 1575, 1465, 1380, 1255, 1235, 1140, 1000, 803 |
| 7 | Light-yellow crystals | 221° (decomp.) | 13 | 0.78 | $C_6H_{18}N_2O_2Cl_2Pt$ | C H N Cl | 17.31 4.36 6.73 17.03 | 17.48 4.41 6.88 17.53 | 3500, 3470, 3190, 2980, 2885, 2440, 1580, 1470, 1400, 1300, 1260, 1140, 1045 |
| 8 | Yellow crystals | 251° (decomp.) | 5 | 0.75 | $C_6H_{16}N_2Cl_4Pt$ | C H N Cl | 15.90 3.56 6.18 31.30 | 16.12 3.60 6.37 31.15 | 3600, 3450, 3250, 3175, 3100, 2975, 2880, 1635, 1575, 1560, 1465, 1450, 1200, 1130, 1020, 880 |
| 9 | White crystals | 230° (decomp.) | 25 | 0.86 | $C_{11}H_{22}N_2O_4Pt$ | C H N | 29.93 5.02 6.35 | 29.90 5.22 6.41 | 3450, 3220, 3110, 2980, 2880, 1660, 1620, 1465, 1375, 1400, 1295, 1235 |
| 10 | White crystals | 248° (decomp.) | 16 | 0.62 | $C_9H_{18}N_2O_5Pt$ | C H N | 25.18 4.23 6.53 | 25.15 4.44 6.69 | 3460, 3180, 3100, 2980, 2840, 1680, 1635, 1465, 1420, 1370, 1300, 1250, 1195, 1130, 930, 760 |
| 11 | Light-yellow crystals | 217° (decomp.) | >2 | 0.78 | $C_7H_{18}N_2O_2Cl_2Pt$ | C H N Cl | 19.63 4.24 6.54 16.54 | 19.82 4.14 6.11 16.22 | 3550, 3530, 3220, 3190, 2950, 2875, 1575, 1560, 1460, 1450, 1275, 1180, 1080, 1015, 850, 715 |
| 12 | Yellow crystals | 254–255° (decomp.) | >15 | 0.80 | $C_7H_{16}N_2Cl_4Pt$ | C H N Cl | 18.08 3.47 6.02 30.49 | 18.27 3.42 6.15 30.59 | 3460, 3280, 3160, 3075, 2980, 2860, 1575, 1545, 1460, 1450, 1210 |
| 13 | White crystals | >300° | >2.5 | 0.67 | $C_9H_{16}N_2O_4Pt$ | C H N | 26.28 3.92 6.81 | 26.03 3.82 6.75 | 3440, 3210, 3140, 2935, 2860, 1705, 1685, 1660, 1595, 1570, 1460, 1380, 1250, 1148, 997, 805 |
| 14 | White powder | 225° | Readily soluble | 0.59 | $C_{10}H_{17}N_2O_5NaPt \cdot 3H_2O$ | C H N | 23.22 4.48 5.42 | 22.96 3.60 5.23 | 3440, 3170, 3100, 2930, 2875, 1665, 1685, 1465, 1370, 1230, 1175, 1080, 950, 738 |
| 15 | White crystals | 170–173° | >1.5 | 0.90 | $C_{11}H_{20}N_2O_4Cl_2Pt$ | C H N | 24.10 4.05 5.62 | 24.38 4.11 5.32 | 3450, 3220, 3150, 2940, 2865, 1708, 1685, 1660, 1660, |

TABLE 1-continued

| No. | Appearance | Melting point (°C.) | Solubility in water (mg/ml) | TLC[1] Rf | Molecular formula | Elementary analysis | | Calcd. % | Found % | IR absorption spectrum (cm$^{-1}$) |
|---|---|---|---|---|---|---|---|---|---|---|
| 16 | White crystals | 263° (decomp.) | >2 | 0.73 | $C_{13}H_{22}N_2O_6Pt$ | C H N | | 31.39 4.46 5.63 | 31.79 4.39 5.33 | 1600, 1563, 1460, 1380, 1250, 1150, 805 3450, 3210, 3110, 2930, 2860, 1630, 1705, 1630, 1590, 1450, 1380, 1210, 1140, 1070, 800, 700 |
| 17 | White crystals | 265° (decomp.) | 8 | 0.84 | $C_{12}H_{22}N_2O_4Pt$ | C H N | | 31.79 4.89 6.18 | 31.85 4.82 6.32 | 3430, 3200, 3100, 2940, 2870, 1630, 1450, 1370, 1340, 1300, 1230, 795 |
| 18 | Yellow crystals | 279° (decomp.) | >3 | 0.63 | $C_6H_{14}N_2Cl_2Pt$ | C H N Cl | | 18.96 3.71 7.37 18.65 | 18.80 3.81 7.19 18.41 | 3470, 3240, 3180, 3110, 2950, 2870, 1580, 1450, 1200, 1185, 1135, 1020, 950, 795 |
| 19 | Light-yellow crystals | 212° (decomp.) | >10 | 0.75 | $C_6H_{16}N_2O_2Cl_2Pt$ | C H N Cl | | 18.86 4.22 7.33 18.55 | 18.97 4.38 7.01 18.35 | 3520, 3170, 3080, 2940, 2875, 1590, 1560, 1455, 1320, 1210, 1060, 1030 |
| 20 | Yellow crystals | >300° Changed to yellow at about 260° C. | 18 | 0.75 | $C_6H_{14}N_2Cl_4Pt$ | C H N Cl | | 15.98 3.13 6.21 31.44 | 16.18 3.21 6.09 31.15 | 3425, 3250, 3200, 3110, 2970, 2880, 1555, 1455, 1395, 1185, 1150, 1110 |
| 21 | White crystals | >300° | >11 | 0.58 | $C_8H_{14}N_2O_4Pt$ | C H N | | 24.19 3.55 7.05 | 24.01 3.67 7.21 | 3400, 3215, 3130, 2960, 2880, 1695, 1672, 1450, 1393, 1300, 1250, 1210, 1160, 1030, 898, 805 |
| 22 | White crystals | 239° (decomp.) | >50 | 0.80 | $C_{11}H_{20}N_2O_4Pt$ | C H N | | 30.07 4.59 6.38 | 30.25 4.81 6.16 | 3460, 3210, 3110, 2975, 2880, 1640, 1450, 1380, 1235, 800 |
| 23 | White crystals | 250° (decomp.) | 5 | 0.55 | $C_9H_{16}N_2O_5Pt$ | C H N | | 25.30 3.77 6.56 | 25.37 3.88 6.77 | 3500, 3200, 3110, 2960, 2880, 1695, 1660, 1460, 1405, 1335, 1240, 1160, 1120, 760 |

[1]adsorption plate: Avicel SF; Developer: BuOH, AcOH, H$_2$O (5:2:3)

As is evident from the above table, the compounds of this invention are relatively rich in water-solubility and hence are suitable for injections and the like.

The compounds of this invention can be produced by any of the following processes (a) to (c).

Process (a):

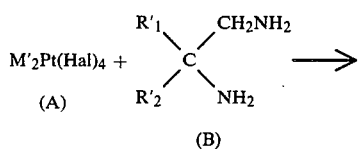

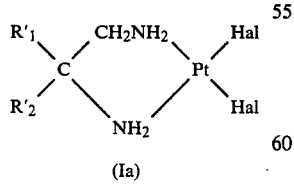

wherein R'$_1$ and R'$_2$ each represents a lower alkyl group having 1 to 3 carbon atoms or jointly represent an alkylene group having 3 to 6 carbon atoms; M' is an alkali metal; and Hal is a halogen atom, and Hal is a halogen atom except chlorine when R'$_1$ and R'$_2$ jointly represent an alkylene group having 5 carbon atoms.

Process (b):

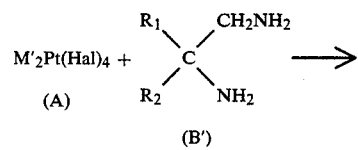

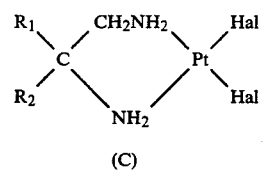

Compound (C) + 2AgNO$_3$ + 2H$_2$O $\longrightarrow$ (2)

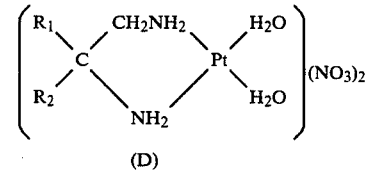

-continued

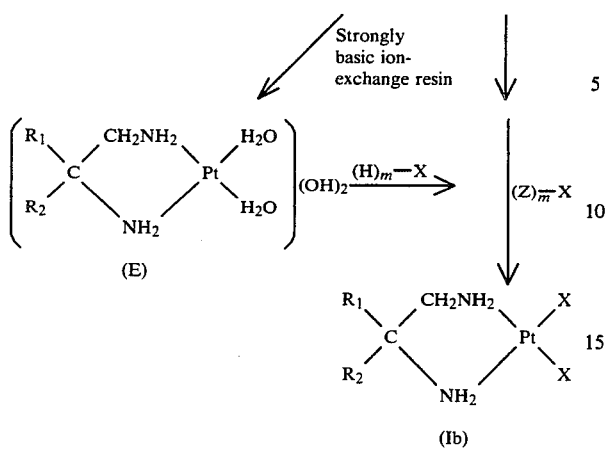

(E)

(Ib)

wherein $R_1$, $R_2$, M' and X are as defined above, Hal is a halogen atom, Z is an atom or a molecule which can become a monovalent or divalent cation, and m is 1 or 2, when X is a halogen atom, Z is an atom or a molecule other than a hydrogen atom, and when $R_1$ and $R_2$ form jointly an alkylene group having 5 carbon atoms, X is a group other than chlorine.

Process (c):

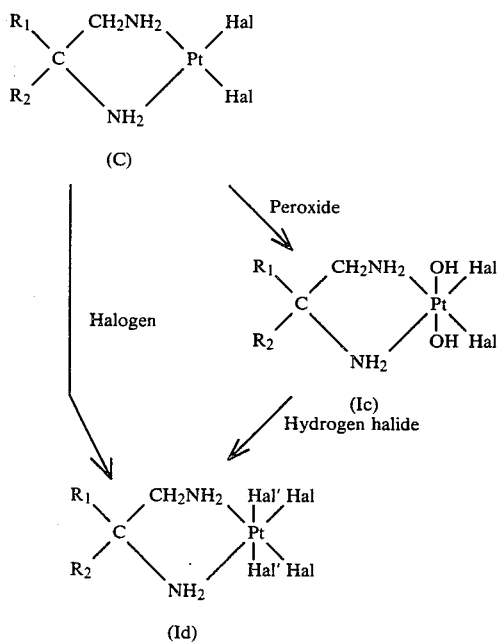

wherein $R_1$ and $R_2$ are as defined above, and Hal and Hal' are the same or different halogen atoms.

The process (a) is suitable for obtaining a compound of the general formula (Ia), i.e., a compound of the general formula (I) in which X is a halogen atom and n is 0. That is to say, by reacting a halogenated platinate (II) of the general formula (A) with a diamine of the general formula (B), there can be obtained a halogenodiammineplatinum of the general formula (Ia), i.e., a compound of the general formula (I) in which $R_1$ and $R_2$ each represents a lower alkyl group having 1 to 3 carbon atoms or jointly represent an alkylene group having 3 to 6 carbon atoms; X is a halogen atom and X is a halogen atom except chlorine when $R_1$ and $R_2$ jointly represent an alkylene group having 5 carbon atoms, and n is 0.

The halogenated platinate (II) includes, for example, alkalimetal salts of chlorinated platinic (II) acid, brominated platinic (II) acid, iodinated platinic (II) acid and fluorinated platinic (II) acid. Among them, potassium halogenoplatinates (II) such as potassium tetrachloroplatinate (II), potassium tetraiodoplatinate (II) and the like are preferred.

The diamine of the general formula (B) includes, for example, those in which each of $R_1$ and $R_2$ is an alkyl group having 1 to 3 carbon atoms, for example, 1,2-diamino-2-methylpropane, 1,2-diamino-2-methylbutane, 1,2-diamino-2-ethylbutane, 1,2-diamino-2-methylpentane, 1,2-diamino-2,3-dimethylbutane 1,2-diamino-2-isopropyl-3-methylbutane and the like, 1-amino-1-aminomethylcyclopentane, etc.

The amount of the diamine to be used is 0.5 to 10 equivalents, preferably 1 to 1.2 equivalents to an equivalent of the halogenated platinic (II) acid or salt thereof. The reaction temperature is 0° to 100° C., preferably 20° to 60° C., and as the reaction time, 5 minutes to 2 hours is needed.

The process (b) can be employed for producing the compound in which n is 0 in general formula (I). That is to say, a diammineplatinum of the general formula (Ib), i.e., a compound of the general formula (I) in which n is 0, can be obtained by reacting the compound (A) with the compound (B') in the same manner as in the above-mentioned process (a) to obtain the compound (C), treating the resulting compound (C) with silver nitrate in an aqueous solution to obtain a solution of aquo complex of the general formula (D), optionally treating the solution of aquo complex with a strongly basic ion-exchange resin to obtain a solution of aquo complex of the general formula (E), and then reacting these aquo complexes with a compound of the general formula:

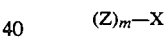

wherein Z, m and X are as defined above. When the solution of aquo complex is treated with a strongly basic ion-exchange resin, (for example, Dowex 1-8X), the resulting solution is reacted with an acid of the formula of $(H)_m$—X, in which m and X are as defined above.

As the halogenated platinate (II) of the general formula (A), there are exemplified the same compounds as exemplified in the case of the above-mentioned process (a), and there are preferably exemplified potassium tetrachloroplatinate (II), potassium tetraiodoplatinate (II), etc.

As the amine of the general formula (B'), there are exemplified 1-amino-1-aminomethylcyclobutane, 1-amino-1-aminomethylcyclohexane, 1-amino-1-aminomethylcycloheptane and the like in addition to the same compounds exemplified in the case of the process (a).

The amounts of compounds of the general formulas (A) and (B') to be used and the reaction conditions are the same as in the process (a).

Next, it is sufficient that the reaction of the compound (C) with silver nitrate is carried out at 0° to 100° C., preferably 20° to 70° C. for 10 minutes to 24 hours. The amount of silver nitrate to be used is one equivalent or less, preferably 0.7 to 1 equivalent, more preferably 0.95 to 0.99 equivalent to an equivalent of the compound of the general formula (C).

The compound of the above general formula $(Z)_m$—X includes, for example, pyruvic acid, chloroacetic acid, methylmalonic acid, ethylmalonic acid, propylmalonic acid, butylmalonic acid, hydroxymalonic acid, oxalic acid, their sodium salts, potassium salts and ammonium salts, and sodium chloride, potassium chloride, etc. The amount of these compounds to be used is one equivalent or more, preferably 1 to 10 equivalents, more preferably 1 to 1.2 equivalents to an equivalent of the compound (A). The reaction temperature is 0° to 100° C., preferably 20° to 60° C., and as the reaction time, 10 minutes to 2 hours is needed.

The process (c) is suitable for obtaining a compound of the general formula:

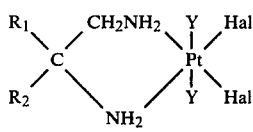

i.e, a compound of the general formula (I) in which X is a halogen atom and n is 1. That is to say, a transdihydroxy derivative of the formula (Ic) corresponding to the formula (I) in which Y is OH can be obtained by reacting a halogenodiammineplatinum of the general formula (C) obtained by the above-mentioned process (a) or (b) with a peroxide.

Further, a trans-dihalo derivative of the formula (Id) corresponding to the formula (I) in which Y is a halogen atom can be obtained by treating the compound of the formula (Ic) with hydrogen halide, or by reacting the compound of the general formula (C) with halogen.

The peroxide includes, for example, hydrogen peroxide, etc. The amount of the peroxide to be used is 2 to 50 equivalents, preferably 5 to 10 equivalents to an equivalent of the compound (C). The reaction temperature is 0° to 100° C., preferably 20° to 90° C., and as the reaction time, 30 minutes to 2 hours is needed.

As the hydrogen halide, there are exemplified hydrogen chloride, hydrogen bromide, hydrogen fluoride and hydrogen iodide, among which hydrogen chloride is preferred. The amount thereof to be used is one equivalent or more, preferably 1 to 10 equivalents, more preferably 1 to 5 equivalents to an equivalent of the compound (Ic). The reaction temperature is 0° to 100° C., preferably 20° to 90° C., and as the reaction time, 10 minutes to 2 hours is needed.

As halogen, there are exemplified, for example, fluorine, chlorine and bromine, among which chlorine is preferred. The amount thereof to be used is 1 to 100 equivalents, preferably 10 to 50 equivalents to an equivalent of the compound (C). The reaction temperature is adequately 50° to 80° C. and the reaction time is 1 to 2 hours.

In the above-mentioned processes (a) to (c), water is usually used as a solvent, and if necessary, these processes are carried out while shielding the light. The crude crystals or crude powder obtained is, if necessary, purified by recrystallization or reprecipitation from hydrochloric acid, water, a water-ethanol mixed solution or the like.

Next, the antitumor effect and acute toxicity of typical compounds of this invention are explained referring to Experimental Example.

EXPERIMENTAL EXAMPLE (1) Test for inhibitory activity on multiplication of mouse leukemia L-1210 initially cultured cells.

Mouse leukemia L-1210 cells collected from the abdominal cavities of DBA/2 mouse were incubated in a 5% $CO_2$ incubator at 37° C. for 48 hours by using a RPMI 1640 medium containing 10% of bovine fetal serum and 5 $\mu$M of 2-mercaptoethanol. Inhibition percentage (%) of multiplication was calculated from the numbers of cells in the case of addition and no addition of each drug, and $IC_{50}$ value (a concentration at which multiplication was inhibited by 50%) was obtained from a graph prepared by plloting a drug concentration and the inhibition percentage on a logarithmic probability paper. The results obtained are shown in Table 2.

TABLE 2

| Compound No. | $IC_{50}$ (mcg/ml) |
|---|---|
| 13 | 0.021 |
| 18 | 0.02 |
| 19 | 0.60 |

(2) Test for antitumor activity on mouse leukemia L-1210.

Into 6-weeks-old female $CDF_1$ mouse were inoculated $1 \times 10^5$ L-1210 cells, and each drug was administered intraperitoneally once a day for 5 consecutive days, starting 24 hours after the inoculation. Physiological saline was administered to a control group. From the average survival periods of the drug-treated group and the control group (abbreviated as T and C, respectively), T/C percentage (T/C×100) was determined.

(3) Acute toxicity test.

Each compound of this invention was intraperitoneally administered 5 times to mouse having L-1210 cancer, and its median letal dose ($LD_{50}$) was determined.

The results of above (2) and (3) are shown in Table 3.

TABLE 3

| Compound No. | Antitumor effect shown by T/C percentage (dose, mg/kg) | | | | | | | | $LD_{50}$ |
|---|---|---|---|---|---|---|---|---|---|
| | (0.5) | (1) | (2) | (4) | (8) | (16) | (32) | (64) | |
| 1 | | 133 | 171 | 206 | 124 | 51 | | | 5.5 |
| 3 | | 127 | 139 | 162 | 154 | 60 | | | 7.5 |
| 5 | 135 | 181 | 291 | 199 | 82 | | | | 3.0 |
| 6 | | 130 | 152 | 226 | 206 | 211 | | | 16.8 |
| 11 | | | | 162 | 237 | 275 | 108 | 67 | 14.0 |
| 12 | 137 | 200 | 259 | 224 | 95 | | | | 3.5 |
| 13 | 146 | 188 | 296 | 230 | 218 | | | | 7.2 |
| 15 | 135 | 175 | 200 | 299 | 130 | | | | 6.0 |
| 18 | 179 | 226 | 344 | 141 | 92 | | | | 3.0 |
| 19 | | | | 138 | 174 | 323 | 113 | 80 | 24.0 |
| 21 | 124 | 141 | 161 | 189 | 166 | | | | 7.6 |

As is evident from Table 3, the compounds of this invention have a high inhibitory effect on growth of mouse leukemia (L-1210) cells and an excellent life prolongation effect on mouse inoculated with L-1210 cells.

(4) Renal toxity test.

Each drug was intraperitoneally administered once to 6-weeks-old $CDF_1$ mouse. Ninety-six hours after the administration, the blood is collected and the blood urea nitrogen concentration (BUN) was determined.

The results are shown in Table 4.

TABLE 4

| Compound No. | Dose (mg/kg) | Weight ratio* | BUN (mg/dl) |
|---|---|---|---|
| Physiological saline | — | 1.05 | 22.7 |
| cis-Platin | 22.6 | 0.76 | 136.6 |
| 1 | 18.0 | 0.88 | 19.3 |
| 3 | 27.0 | 0.84 | 18.6 |
| 5 | 30.4 | 0.73 | 25.1 |
| 11 | 144.0 | 0.72 | 21.9 |
| 12 | 36.0 | 0.72 | 18.0 |
| 13 | 20.3 | 0.76 | 16.5 |
| 15 | 35.6 | 0.75 | 17.2 |
| 18 | 30.4 | 0.77 | 16.5 |
| 19 | 108.0 | 0.91 | 18.8 |
| 21 | 45.0 | 0.89 | 25.3 |

*Ratio of the body weight on the drug administration day to the body weight at 96 hours after the administration.

As is evident from Table 4, the compounds of this invention bring about a greatly lowered BUN value which is one-fifth or less as much as that brought about by commercially available cis-Platin, and substantially equal to or smaller than that brought about by physiological saline, and it can be seen that said compounds are very low in renal toxicity.

The compound of this invention is, therefore, expected as an antitumor agent having a very low renal toxicity. When used as an antitumor agent, the compound of this invention is intravenously administered usually in the form of an injection, and its dosage is about 1 to 80 mg/m$^2$ (surface area of human body) a time.

The process for producing the compound of this invention is explained below with reference to Examples.

EXAMPLE 1 cis-Dichloro-1,2-diamino-2-methylpropane platinum (compound No. 1).

In 3.5 ml of water was dissolved 207.6 mg of potassium tetrachloroplatinate (II), and a solution of 45 mg of 1,2-diamino-2-methylpropane dissolved in 1.5 ml of water was added dropwise with stirring. The resulting mixture was subjected to reaction at room temperature for 1.5 hours and then cooled for 4 days, and the crystals deposited was collected by filtration, washed with water, and then dried to obtain 126 mg of crude crystals of compound No. 1. The crude crystals were recrystalized from 4.5 ml of hot water to obtain 50.9 mg of compound No. 1 in a pure form.

EXAMPLE 2 cis-Dichloro-1,2-diamino-2-ethylbutane platinum (compound No. 5).

In 20 ml of water was dissolved 2.08 g of potassium tetrachloroplatinate (II), after which a solution of 3.42 g of potassium iodide dissolved in 5 ml of water was added dropwise, and the resulting mixture was subjected to reaction with stirring at 40° C. for 10 minutes to obtain a black solution of potassium tetraiodoplatinate (II). A solution of 638 mg of 1,2-diamino-2-ethylbutane dissolved in 15 ml of water was added dropwise to the black solution, and the resulting mixture was stirred at room temperature for 2 hours. The deposited precipitate was collected by filtration, washed with water, and then dried to obtain 2.77 g of yellowish-brown powder of cis-diiodo-1,2-diamino-2-ethylbutane platinum. In 22.5 ml of water was suspended 2.77 g of the resulting diiods compound, and 1.64 g of silver nitrate was added, after which the resulting mixture was subjected to reaction with stirring at 65° C. for 10 minutes and then at room temperature for 1 hour and thereafter filtered, and the silver iodide on the filter was washed with water.

The filtrate and the washings were combined, and 0.795 g of potassium chloride was added with stirring, after which the resulting mixture was allowed to stand at 40° C. for 10 minutes and then in a cold place for 2 hours, and the deposited crystals were collected by filtration, washed with water, and then dried to obtain 1.36 g of crude crystals of compound No. 5.

The crude crystals were recrystallized from 110 ml of 0.1N hydrochloric acid to obtain 1.10 g of compound No. 5 in a pure form.

EXAMPLE 3 cis-Dichloro-1-amino-1-aminomethylcyclopentane platinum (compound No. 18).

Reaction was conducted in the same manner as in Example 2, except that 793 mg of 1-amino-1-aminomethylcyclopentane was used in place of 1,2-diamino-2-ethylbutane, to obtain 1.38 g of crude crystals of compound No. 18. The crude crystals were recrystallized from 110 ml of 0.1N hydrochloric acid to obtain 930 mg of compound No. 18 in a pure form.

EXAMPLE 4 cis-Dichloro-trans-dihydroxy-1,2-diamino-2-methylpropane platinum (compound No. 2).

In 5 ml of water was suspended 1 g of compound No. 1, after which 3.6 ml of a 30% aqueous hydrogen peroxide solution was added dropwise with stirring, and the resulting solution was subjected to reaction at room temperature for 2 hours. The reaction solution was ice-cooled for 1 hour, and the deposited solid was collected by filtration, washed with water, and then dried to obtain 605.4 mg of crude crystals of compound No. 2. The crude crystals were dissolved in 24 ml of hot water, and 75 ml of acetone was added, after which the resulting mixture was ice-cooled, and after two hours, the precipitate was collected by filtration and then dried to obtain 542.7 mg of compound No. 2 in a pure form.

EXAMPLE 5 cis-Dichloro-trans-dihydroxy-1-amino-1-aminomethylcyclohexane platinum (compound No. 11).

(1) Reaction was conducted in the same manner as in Example 2, except that 1.41 g of 1-amino-1-aminomethylcyclohexane was used in place of 1,2-diamino-2-ethylbutane, to obtain 1.59 g of crude crystals of cis-dichloro-1-amino-1-aminomethylcyclohexane platinum. The crude crystals were dissolved in 10 ml of dimethylformamide, and the resulting solution was filtered. Thereafter, 40 ml of methanol was added to the filtrate and the resulting mixture was ice-cooled, after which the precipitate was collected by filtration, washed with methanol, and then dried to obtain 1.34 g of the product in a pure form.

(2) Reaction was conducted in the same manner as in Example 4, except that 1 g of the platinum complex obtained in (1) was used in place of the compound No. 1 in Example 4, to obtain 640 mg of compound No. 11 in a pure form.

EXAMPLE 6 cis-Dichloro-trans-dihydroxy-1-amino-1-aminomethylcyclopentane platinum (compound No. 19).

Reaction was conducted in the same manner as in Example 4, except that 1.0 g of compound No. 18 was used in place of compound No. 1, to obtain 537 mg of compound No. 19.

EXAMPLE 7 cis-Tetrachloro-1,2-diamino-2-methylpropane platinum (compound No. 3).

In 14.3 ml of 0.2N hydrochloric acid, 489 g of compound No. 2 was stirred at 80° C. for 30 minutes. This reaction solution was concentrated to a volume of 2.5 ml, after which the concentrate was ice-cooled for 1 hour, and the precipitate was collected by filtration, washed with water, and then dried. There was obtained 437.1 mg of crude crystals of compound No. 3. The crude crystals were recrystallized from 5 ml of 0.1N hydrochloric acid to obtain 169.3 mg of compound No. 3 in a pure form.

EXAMPLE 8 cis-Tetrachloro-1-amino-1-aminomethylcyclohexane platinum (compound No. 12).

In 0.5 ml of water was suspended 100 mg of compound No. 11, after which 0.2 ml of 36% hydrochloric acid was added dropwise, and the reaction solution was stirred at 70° to 75° C. for 15 minutes. It was then ice-cooled and the precipitate was collected by filtration, washed with water, and then dried to obtain 79 mg of compound No. 12 in a pure form.

EXAMPLE 9 cis-Oxalato-1-amino-1-aminomethylcyclohexane platinum (compound No. 13).

A mixture of 39.4 mg of the platinum complex obtained by the process of Example 5-(1), 333 mg of silver nitrate and 10 ml of water was stirred at room temperature for 4 hours, after which the reaction mixture was filtered and the residue was washed with water. The filtrate and the washings were combined, followed by adding thereto a solution prepared by dissolving 1.51 mg of oxalic acid dihydrate dissolved in 2 ml of water and neutralizing the resulting solution to about pH6 with a 30% aqueous sodium hydroxide solution. The resulting mixture was stirred at room temperature for 3 hours and then at 60° to 65° C. for 1 hour. This mixture was ice-cooled and the precipitate was collected by filtration, washed with water, and then dried to obtain 295 mg of light-gray crystals of compound No. 13. The crystals were dissolved in 150 ml of methanol with heating and the resulting solution was treated with active carbon, after which most of the methanol was distilled off, and the residue was cooled, separated by filtration, washed with methanol, and then dried to obtain 239 mg of white crystals of compound No. 13.

EXAMPLE 10 cis-Oxalato-1-amino-1-aminomethylcyclopentane platinum (compound No. 21).

Reaction was conducted in the same manner as in Example 9, except that compound No. 18 was used in place of the platinum complex obtained in Example 5-(1), to obtain 213 mg of light-gray crystals of compound No. 21. The crystals were dissolved in 64 ml of methanol with heating and then treated in the same manner as in Example 9 to obtain 182 mg of white crystals of compound No. 21.

EXAMPLE 11 cis-Oxalato-1,2-diamino-2-ethylbutane platinum (compound No. 6).

Reaction was conducted in the same manner as in Example 9, except that 382 mg of compound No. 5 was used in place of the platinum complex obtained in Example 5-(1), to obtain 270 mg of gray crystals of compound No. 6. The crystals were dissolved in 81 ml of methanol with heating and then treated in the same manner as in Example 9 to obtain 180 mg of white crystals.

EXAMPLE 12 cis-Dichloro-1,2-diamino-2-methylbutane platinum (compound No. 4).

Reaction was conducted in the same manner as in Example 2, except that 1,2-diamino-2-methylbutane was used in place of 1,2-diamino-2-ethylbutane, to obtain 1.44 g of crude crystals of compound No. 4. The crude crystals were recrystallized from 60 ml of 0.1N hydrochloric acid to obtain 780 mg of pure crystals.

EXAMPLE 13 cis-Dichloro-trans-dihydroxy-1,2-diamino-2-ethylbutane platinum (compound No. 7).

Reaction was conducted in the same manner as in Example 4, except that compound No. 5 was used in place of compound No. 1, to obtain 512 mg of crystals of compound No. 7.

EXAMPLE 14 cis-Tetrachloro-1,2-diamino-2-ethylbutane platinum (compound No. 8).

In 4 ml of water was suspended 832 mg of compound No. 7 obtained by the process of Example 13, after which 1.7 ml of 35% hydrochloric acid was added, and the resulting mixture was stirred at 80° C. for 30 minutes. After being ice-cooled, the mixture was filtered, and the residue was washed with water, and then dried to obtained 818 mg of crystals of compound No. 8.

EXAMPLE 15 cis-Tetrachloro-1-amino-1-aminomethylcyclopentane platinum (compound No. 20).

Reaction was conducted in the same manner as in Example 14, except that compound No. 19 was used in place of compound No. 7. The reaction solution was allowed to stand for 3 days to deposit yellow crystals. The formed crystals were collected by filtration, washed with water, and then dried to obtain 582 mg of crystals of compound No. 20.

EXAMPLE 16

Sodium salt of cis-2-hydroxymalonato-1-amino-1-aminomethylcyclohexane platinum (compound No. 14).

In 3 ml of water was suspended 349 mg of the platinum complex obtained in Example 5-(1), after which 333 mg of silver nitrate was added, and the resulting mixture was stirred at room temperature for 4 hours. The reaction mixture was filtered and the residue was washed with water. The filtrate and the washings were combined, followed by adding thereto a solution prepared by dissolving 144 mg of 2-hydroxymalonic acid in 1 ml of water and neutralizing the resulting solution to pH6 with 30% aqueous sodium hydroxide solution. The resulting mixture was stirred at room temperature for 1 hour and then at 50° to 60° C. for 30 minutes, and thereafter ice-cooled, and the precipitate was collected by filtration, washed with water, and then dried to obtain 356 mg of cis-2-hydroxymalonato-1-amino-1-aminomethylcyclohexane platinum.

The resulting compound was suspended in 15 ml of water, and 0.67 ml 1N sodium hydroxide solution was added to dissolve the compound. The resulting solution was filtered, after which the filtrate was concentrated and then dried, and 10 ml of acetone was added. The resulting mixture was stirred and then filtered, and the resulting residue was washed with acetone to obtain 288 mg of compound No. 14.

EXAMPLE 17 cis-bis(Chloroacetato)-1-amino-1-aminomethylcyclohexane platinum (compound No. 15).

A mixture of 394 mg of the platinum complex obtained in Example 5-(1), 333 mg of silver nitrate and 6 ml of water was stirred at room temperature for 4 hours and then filtered, and the precipitate on the filter was washed with water. The filtrate and the washings were combined, followed by adding thereto a solution prepared by dissolving 286 mg of chloroacetic acid in 1 ml of water and neutralizing the resulting solution to pH7 with 30% sodium hydroxide solution. The resulting mixture was stirred at room temperature for 3 hours and then at 60° to 65° C. for 1 hour. The mixture was then ice-cooled, and the formed precipitate was collected by filtration, washed with water, and then dried to obtain 357 mg of crystals of compound No. 15. The crystals were dissolved in 36 ml of methanol with heating, after which the resulting solution was treated with active carbon, concentrated, ice-cooled and then filtered, and the resulting residue was washed with methanol to obtain 221 mg of white crystals.

EXAMPLE 18 cis-Bispyruvato-1-amino-1-aminomethylcyclohexane platinum (compound No. 16).

A mixture of 394 mg of the platinum complex obtained in Example 5-(1), 333 mg of silver nitrate and 6 ml of water was stirred at room temperature for 4 hours and then filtered, and the precipitate on the filter was washed with water. The filtrate and the washings were combined and then passed through a column packed with an anion-exchange resin Dowex 1-8X ® (OH type, manufactured by Dow Chemical Corp.). To the resulting aqueous solution was added 176 mg of pyruvic acid, and the resulting mixture was allowed to stand overnight. The solution was then concentrated and the residue was dissolved in 10 ml of ethanol, after which the resulting solution was ice-cooled, and the formed precipitate was collected by filtration, washed with ethanol, and then dried to obtain 70 mg of light-yellow crystals of compound No. 16.

EXAMPLE 19 cis-2-Ethylmalonato-1,2-diamino-2-ethylbutane Platinum (compound No. 9).

In 8.5 ml of water was suspended 1.70 g of cis-diiodo-1,2-diamino-2-ethylbutane platinum obtained in Example 2, and 1.00 g of silver nitrate was added, after which the temperature was slowly raised to 50° C., and the mixture was stirred at 50° to 55° C. for 30 minutes. After the mixture was cooled to room temperature, the deposited silver iodide was filtered off. To the filtrate obtained was added a solution prepared by dissolving 436 mg of 2-ethylmalonic acid in 1.5 ml of water and neutralizing the resulting solution to pH6. The resulting solution was stirred at 50° to 55° C. Thereafter, the solution was treated with active carbon, concentrated to a volume of about 5 ml, and then ice-cooled, after which the deposited crystals were collected by filtration, washed with water, and then dried to obtain 828 mg of white crystals of compound No. 9.

EXAMPLE 20 cis-2-Hydroxymalonato-1,2-diamino-2-ethylbutane platinum (compound No. 10).

Reaction was conducted in the same manner as in Example 19, except that 380 mg of hydroxymalonic acid was used in place of 2-ethylmalonic acid, to form a white precipitate. After ice-cooling, the formed precipitate was collected by filtration, washed with water, and then dried to obtain 317 mg of crystals of compound No. 10. The filtrate was concentrated to a volume of about 2 ml to obtain 108 mg of crystals of compound No. 10 additionally. Both the former and the latter crystals were dissolved in 12 ml of water and filtered, and 36 ml of methanol was added to the filtrate, after which the resulting mixture was ice-cooled, and the deposited crystals were collected by filtration, washed with methanol, and then dried to obtain 283 mg of compound No. 10 in a pure form.

EXAMPLE 21 cis-2-Ethylmalonato-1-amino-1-aminomethylcyclopentane platinum (compound No. 22).

Reaction was conducted in the same manner as in Example 19, except that 1.69 g of cis-diiodo-1-amino-1-aminomethylcyclopentane platinum was used in place of cis-diiodo-1,2-diamino-2-ethylbutane platinum. The reaction mixture was treated with active carbon and then concentrated to a volume of about 10 ml, and 60 ml of acetone was added, after which the resulting mixture was cooled, and the deposited crystals were collected by filtration and washed with acetone to obtain 591 mg of white crystals of compound No. 22.

EXAMPLE 22 cis-2-Hydroxymalonato-1-amino-1-aminomethylcyclopentane platinum (compound No. 23).

Reaction was conducted in the same manner as in Example 20, except that 1.69 g of cis-diiodo-1-amino-1-aminomethylcyclopentane platinum was used in place of cis-diiodo-1,2-diamino-2-ethylbutane platinum. The formed precipitate was collected by filtration after ice-cooling, washed with water, and then dried to obtain 743 mg of light-brown crystals. The crystals were dissolved in 75 ml of water with heating, after which the resulting solution was treated with active carbon, concentrated to a volume of about 15 ml, and then cooled, and the deposited crystals were collected by filtration, washed with water, and then dried to obtain 592 mg of white crystals of compound No. 23.

EXAMPLE 23 cis-2-Ethylmalonato-1-amino-1-aminomethylcyclohexane platinum (compound No. 17).

Reaction was carried out in the same manner as in Example 19, except that 1.73 g of cis-diiodo-1-amino-1-aminomethylcyclohexane platinum was used in place of cis-diiodo-1,2-diamino-2-ethylbutan platinum, to form a white precipitate. After cooling, the crystals were collected by filtration, washed with water, and then dried to obtain 645 mg of crystals of compound No. 17. The crystals thus obtained were dissolved in 52 ml of water with heating, and the resulting solution was treated with active carbon, concentrated to a volume of about 15 ml, and then cooled, and the deposited crystals were collected by filtration, washed with water, and then dried to obtain 355 mg of white crystals of compound No. 17.

EXAMPLE 24 cis-Tetrachloro-1-amino-1-aminomethylcyclohexane platinum (compound No. 12)

In 5 ml of water was suspended 400 mg of cis-dichloro-1-amino-1-aminomethylcyclohexane platinum (II), and chlorine gas was bubbled therethrough at 70° C. for about 1 hour. Subsequently, the reaction mixture was cooled, and the deposited crystals were collected by filtration, washed with water, and then dried to obtain 250 mg of yellow crystals of compound No. 12.

What is claimed is:
1. cis-Dichloro-1,2-diamino-2-methylpropane platinum.
2. cis-Tetrachloro-1,2-diamino-2-methylpropane platinum.
3. cis-Dichloro-1,2-diamino-2-ethylbutane platinum.
4. cis-Oxalato-1,2-diamino-2-ethylbutane platinum.
5. cis-Dichloro-trans-dihydroxy-1-amino-1-aminomethylcyclohexane platinum.
6. cis-Tetrachloro-1-amino-1-aminomethylcyclohexane platinum.
7. cis-Oxalato-1-amino-1-aminomethylcyclohexane platinum.
8. cis-Bis(chloroacetato)-1-amino-1-aminomethylcyclohexane platinum.
9. cis-Dichloro-1-amino-1-aminomethylcyclopentane platinum.
10. cis-Dichloro-trans-dihydroxy-1-amino-1-aminomethylcyclopentane platinum.
11. cis-Oxalato-1-amino-1-aminomethylcyclopentane platinum.
12. Cis-Dichloro-trans-dihydroxy-1,2-diamino-2-ethylbutane platinum.
13. Cis-2-Ethylmalonato-1,2-diamino-2-ethylbutane platinum.

* * * * *